United States Patent [19]

Gruenberg

[11] Patent Number: 5,763,261
[45] Date of Patent: *Jun. 9, 1998

[54] CELL GROWING DEVICE FOR IN VITRO CELL POPULATION EXPANSION

[75] Inventor: Michael Gruenberg, Minneapolis, Minn.

[73] Assignee: CellTherapy, Inc., San Diego, Calif.

[*] Notice: The term of this patent shall not extend beyond the expiration date of Pat. No. 5,627,070.

[21] Appl. No.: 759,645

[22] Filed: Dec. 5, 1996

Related U.S. Application Data

[63] Continuation of Ser. No. 506,173, Jul. 26, 1995, Pat. No. 5,627,070.
[51] Int. Cl.⁶ .................. C12M 3/06; C12N 5/00
[52] U.S. Cl. .................. 435/286.5; 435/286.6; 435/297.4; 435/3; 435/400; 435/294.1
[58] Field of Search .................. 435/286.5, 294.1, 435/297.1, 297.2, 297.4, 286.1, 286.6, 395, 398, 400, 401, 3; 422/48; 210/321.8, 321.89, 323.2, 340

[56] References Cited

U.S. PATENT DOCUMENTS

| | | | |
|---|---|---|---|
| 3,883,393 | 5/1975 | Knazek et al. | 195/1.8 |
| 4,266,026 | 5/1981 | Breslau | 435/99 |
| 4,690,915 | 9/1987 | Rosenberg | 514/2 |
| 4,722,902 | 2/1988 | Harm et al. | 435/284 |
| 4,804,628 | 2/1989 | Cracauer et al. | 435/240 |
| 4,889,812 | 12/1989 | Guinn et al. | 435/289 |
| 5,057,423 | 10/1991 | Hiserodt et al. | 435/240 |
| 5,126,132 | 6/1992 | Rosenberg | 424/93 |
| 5,199,942 | 4/1993 | Gillis | 604/4 |
| 5,229,115 | 7/1993 | Lynch | 424/93 |
| 5,424,209 | 6/1995 | Kearney | 435/284 |
| 5,627,070 | 5/1997 | Gruenberg | 435/297.4 |

FOREIGN PATENT DOCUMENTS

| | | | |
|---|---|---|---|
| 480400 | 4/1992 | European Pat. Off. | 435/297.4 |
| 61-254184 | 11/1986 | Japan | 435/297.4 |
| 1747479 | 7/1992 | U.S.S.R. | 435/297.4 |
| WO 86/02379 | 4/1986 | WIPO | |

OTHER PUBLICATIONS

G. DelPrete, A. Tiri, M. DeCarli, S. Mariotti, A. Pincheara, I. Chretien, S. Romagnani, and M. Ricci, High Potential to Tumor Necrosis Factor X (INF-x) Production of Thyroid–Infiltrating T Lymphocytes in Hashimoto's Thyroiditis: A Peculiar Feature of Destructive Thyroid Autoimmunity, *Autoimmunity*, 4:267 (1989).

E.J. Davis, D.O. Cooney, and R. Chang, Mass Transfer Between Capillary Blood and Tissues, *Chem. Eng. J.*, 7:213 (1974).

J. Igietseme, K. Ramsey, D. Magee, D. Williams, J. Kincy, and R. Rank, Resolution of Marine Chlamydial Genital Infection by the Adoptive Transfer of a Biovar–Specific, TH1 Lymphocyte Clone, *Regional Immunol.*, 5:317 (1993).

T. Whiteside, E. Elder, O. Moody et al., Generation and Characterization of Ex-Vivo Propagated Autologous CD8T Cells Used for Adoptive Immunotherapy of Patients Infected With Human Immunodeficiency Virus, *Blood*, 81:2085 (1993).

(List continued on next page.)

*Primary Examiner*—William H. Beisner
*Attorney, Agent, or Firm*—Kinney & Lange, P.A.

[57] ABSTRACT

A cell growing device for in vitro cell population growth includes at least one hollow fiber cartridge having a plurality of capillaries at least one of which is selectively permeable. The flow of media out of a lumen of the cartridge is substantially blocked off thereby forcing media flowing into the lumen via an inflow opening to permeate across the capillaries of the cartridge and into the extracapillary space thereof.

24 Claims, 5 Drawing Sheets

OTHER PUBLICATIONS

N. Klimas, R. Patarca, J. Walling, R. Garcia, V. Mayer, D. Moody, T. Okarma and M. Fletcher, Clinical and Immunological Changes in AIDS Patients Following Adoptive Therapy with Activated Autologous CD8 T Cells and Interleukin-2 Infusion, *Aids*, vol. 8, pp. 1073–1081, 1994.

S. Riddell, M. Gilbert and P. D. Greenberg, CD8$^+$Cytotoxic T Cell Therapy of Cytomegalovirus and HIV Infection, *Current Opinion in Immunology*, vol. 5, pp. 484–491, 1993.

D. Torpey III, X. Huang, J. Armstrong, M. Ho, T. Whiteside, D. McMahon, G. Pazin, R. Herberman, P. Gupta, C. Tripoli, D. Moody, T. Okarma, E. Elder, and C. Rinaldo, Jr., Effects of Adoptive Immunotherapy with Autologous CD8$^+$T Lymphocytes on Immunologic Parameters: Lymphocyte Subsets and Cytotoxic Activity, *Clinical Immunology and Immunopathology*, vol. 68, No. 3, pp. 263–272, Sep. 1993.

M. Ho, J. Armstrong, D. McMahon, G. Pazin, X. Li Huang, C. Rinaldo, T. Whiteside, C. Tripoli, G. Levine, D. Moody, T. Okarma, E. Elder, P. Gupta, A Phase 1 Study of Adoptive Transfer of Autologous CD8$^+$T Lymphocytes in Patients With Acquired Immunodeficiency Syndrome (AIDS)–Related Complex or Aids, *Blood*, vol. 81, No. 8, pp. 2093–2101, Apr. 15, 1993.

S. Riddell, K. Watanabe, J. Goodrich, C. Li, M. Agha, P. Greenberg, Restoration of Viral immunity in Immunodeficient Humans by the Adoptive Transfer of T Cell Clones, *Science*, vol. 257, pp. 238–241, Jul. 10, 1992.

L. Romani, S. Mocci, C. Bietta, L. Lanfaloni, P. Puccetti, and F. Bistoni, Th1 and Th2 Cytokine Secretion Patterns in Murine Candidiasis: Association of Th1 Responses with Acquired Resistance, *Infection and Immunity*, vol. 54, No. 12, pp. 4647–4654, Dec. 1991.

A. Saoudi, J. Kuhn, K. Huygen, Y. Kozak, T. Velu, M. Goldman, P. Druet, and B. Bellon, TH2 Activated Cells Prevent Experimental Autoimmune Uveoretinitis, a TH1–Dependent Autoimmune Disease, *Eur. J. Immunol.*, vol. 23, pp. 3096–3103, 1993.

E. Grimm, A. Mazumder, H. Zhang, and S. Rosenberg, Lymphokine–Activated Killer Cell Phenomenon, *Journal of Experimental Medicine*, vol. 155, pp. 1823–1841, Jun. 1982.

S. Rosenberg, M. Lotze, L. Muul, A. Chang, F. Avis, S. Leitman, W. Linehan, G. Robertson, R. Lee, J. Rubin, C. Seipp, C. Simpson, and D. White, A Progress Report on the Treatment of 157 Patients with Advanced Cancer Using Lymphokine–Activated Killer Cells and Interleukin–2 or High–Dose Interleukin–2 Alone, *The New England Journal of Medicine*, vol. 316, No. 15, pp. 889–897, Apr. 9, 1987.

S. Rosenberg, M. Lotze, L. Muul, S. Leitman, A. Chang, S. Ettinghausen, Y. Matory, J. Skibber, E. Shiloni, J. Vetto, C. Seipp, C. Simpson, and C. Reichert, Observations on the Systemic Administration of Autologous Lymphokine–Activated Killer Cells and Recombinant Interleukin–2 to Patients with Metastatic Cancer, *The New England Journal of Medicine*, vol. 313, No. 23, pp. 1485–1490, Dec. 5, 1985.

J. Eastcott, K. Yamashita, M. Taubman, Y. Harada, D. Smith, Adoptive Transfer of Cloned T Helper Cells Ameliorates Periodontal Disease in Nude Rats, *Oral Microbiology and Immunology*, vol. 9, pp. 284–289, 1994.

P. Thygesen, L. Brandt, T. Jorgensen, H. Christensen, H. Hougen, E. Jensen, J. Rygaard, Immunity to Experimental Salmonella Typhimurium Infections in Rats, *APMIS*, vol. 102, pp. 489–494, 1994.

T. Utsugi, M. Nagata, T. Kawamura, and J. Yoon, Prevention of Recurrent Diabetes in Syngenic Islet–Translanted Nod Mice by Transfusion of Autoreactive T Lymphocytes, *Transplanation*, vol. 57, 1799–1804, No. 12, pp. 1799–1804, Jun. 1994.

F. Powrie, R. Correa–Oliveira, S. Mauze, and R. Coffman, Regulatory Interactions Between CD45RB$^{high}$ and CD45RB$^{low}$ CD4+ T Cells Are Important for the Balance Between Protective and Pathogenic Cell–mediated Immunity, *J. Exp. Med.*, vol. 179, pp. 589–600, Feb. 1994.

R. Dillman, R. Oldham, K. Tauer, D. Orr, N. Barth, G. Blumenschein, J. Arnold, R. Birch, and W. West, Continuous Interleukin–2 and Lymphokine–Activated Killer Cells for Advanced Cancer: A National Biotherapy Study Group Trial, *Journal of Clinical Oncology*, vol. 9, No. 7, pp. 1233–1240, Jul. 1991.

J. Thompson, K. Shulman, M. Benyunes, C. Lindgren, C. Collins, P. Lange, W. Bush, Jr., L. Benz, and A. Fefer, Prolonged Continuous Intravenous Infusion Interleukin–2 and Lymphokine–Activated Killer–Cell Therapy for Metastatic Renal Cell Carcinoma, *Journal of Clinical Oncology*, vol. 10, No. 6, pp. 960–968, Jun. 1992.

K. Foon, P. Walther, Z. Bernstein, L. Vaickus, R. Rahman, H. Watanabe, J. Sweeney, J. Park, D. Vesper, D. Russell, R. Walker, T. Darrow, T. Linna, D. Farmer, W. Lynch, Jr., R. Huben, and M. Goldrosen, Renal Cell Carcinoma Treated with Continuous–Infusion Interleukin–2 with Ex Vivo–Activated Killer Cells, *Journal of Immunotherapy*, vol. 11, No. 3, pp. 184–190, 1992.

M. Koretz, D. Lawson, M. York, S. Graham, D. Murray, T. Gillespie, D. Levitt, and K. Sell, Randomized Study of Interleukin 2 (IL–2) Alone vs IL–2 Plus Lymphokine–Activated Killer Cells for Treatment of melanoma and Renal Cell Cancer, *Arch Surg*, vol. 126, pp. 898–903, Jul. 1991.

P. Sedlmayr, H. Rabinowich, E. Elder, M. Ernstoff, J. Kirkwood, R. Herberman, and T. L. Whiteside, Depressed Ability of Patients with Melanoma or Renal Cell Carcinoma to Generate Adherent Lymphokine–Activated Killer Cells, *Journal of Immunotherapy*, vol. 10, No. 5, pp. 336–346, 1991.

M. Sacchi, D. Vitolo, P. Sedlmayr, H. Rabinowich, J. Johnson, R. Herberman, and T. Whiteside, Induction of Tumor Regression in Experimental Model of Human and Neck Cancer by Human A–Lak Cells and IL–2, *Int. J. Cancer*, vol. 47, pp. 784–791, 1991.

S. Rosenberg, B. Packard, P. Aebersold, D. Solomon, S. Topalian, S. Toy, P. Simon, M. Lotze, J. Yang, C. Seipp, C. Simpson, C. Carter, St. Bock, D. Schwartzentruber, J. Wei, and D. White, Use of Tumor–Infiltrating Lymphocytes and Interleukin–2 in the Immunotherapy of Patients with Metastatic Melanoma, *The New England Journal of Medicine*, vol. 319, No. 25, pp. 1676–1680, Dec. 22, 1988.

R. Dillman, R. Oldham, N. Barth, R. Cohen, D. Minor, R. Birch, J. Yannelli, J. Maleckar, A. Sferruzz, J. Arnold, and W. West, Continuous Interleukin–2 and Tumor–Infiltrating Lymphocytes as Treatment of Advanced Melanoma, *Cancer*, vol. 68, pp. 1–8, Jul. 1, 1991.

S. Huet, H. Wakasugi, G. Sterkers, J. Gilmour, T. Tursz, L. Boumsell, and A. Bernard, T Cell Activation VIA CD2 [T, gp50]: The Role of Accessory Cells in Activating Resting T Cells VIA CD2, *The Journal of Immunology*, vol. 137, No. 5, pp. 1420–1428, Sep. 1, 1986.

F. Spertini, T. Chatila, and R. Geha, Signals Deliverd Via MHC Class II Molecules Synergize with Signals Delivered Via TCR/CD3 to Cause Proliferation and Cytokine Gene Expression in T Cells, *Journal of Immunology*, vol. 149, No. 1, pp. 65–70, Jul. 1, 1992.

R. Galandrini, N. Albi, G. Tripodi, D. Zarcone, A. Terenzi, A Moretta, C. Grossi, and A. Velardi, Antibodies to CD44 Trigger Effector Functions of Human T Cell Clones, *The Journal of Immunology*, vol. 150, No. 10, pp. 4225–4235, May 15, 1993.

B. Manger, A. Weiss, C. Weyand, J. Goronzy, and J. Stobo, T Cell Activation: Differences in the Signals Required for IL 2 Production by Nonactivated and Activated T Cells, *The Journal of Immunology*, vol. 135, No. 6, pp. 3669–3673, Dec. 1985.

T. Hara, S. Fu, and J. Hansen, Human T Cell Activation, *J. Exp. Med.*, vol. 161, pp. 1513–1524, Jun. 1985.

Y. Shimizu, G. Van Seventer, K. Horgan, and S. Shaw, Costimulation of Proliferative Responses of Resting $CD4^+T$ Cells by the Interaction of VLA–4 and VLA–5 with Fibronectin or VLA–6 with Laminin, *The Journal of Immunology*, vol. 145, No. 1, pp. 59–67, Jul. 1, 1990.

Cell Culture on Artificial Capillaries: An Approach to Issue Growth In Vitro, *Science*, vol. 176, pp. 65–67, Oct. 1972.

P. Gullino and R. Knazek, Tissue Culture on Artificial Capillaries, *Methods in Enzymology*, vol. LVIII, pp. 178–185, 1979.

R. Knazek, P. Kohler, and P. Gullino, Hormone Production by Cells Grown In Vitro on Artificial Capillaries, *Experimental Cell Research 84*, pp. 251–254, 1974.

Beta Cell Culture on Synthetic Capillaries: An Artificial Encocrine Pancreas, *Science*, vol. 187, pp. 847–849, Mar. 1975.

J. Hager, S. Spiegelman, M. Ramanarayanan, J. Bausch, P. Galletti, and P. Calabresi, Tumor–Associated Antigens Produced by Mouse Mammary Tumor Cells in Artificial Capillary Culture, *JNCI*, vol. 69, No. 6, pp. 1359–1365, Dec. 1982.

R. Knazek, M. Lippman, and H. Chopra, Brief Communication: Formation of Solid Human Mammary Carcinoma In Vitro, *J. National Cancer*, vol. 58, No. 2, pp. 419–422, Feb. 1977.

L. Rutzky, J. Tomita, and M. Calenoff, Human Colon Adenocarcinoma Cells. III. In Vitro Organoid Expression and Carcinoembryonic Antigen Kinetics in Hollow Fiber Culture, *JNCI*, vol. 63, No. 4, pp. 893–902, Oct. 1979.

G. David, R. Reisfeld, and T. Chino, Continuous Production of Carcinoembryonic Antigen in Hollow Fiber Cell Culture Units: Brief Communication, *J Natl Cancer Inst.*, vol. 60, No. 2, pp. 303–306, Feb. 1978.

C. Wolf, and B. Munkelt, Bilirubin Conjugation By an Artificial Liver Composed of Cultured Cells and Syntetic Capillaries, *Trans. Amer. Soc. Artif. Int. Organs*, vol. XX1, pp. 16–27, 1975.

W. Tze, and L. Chen, Long–Term Survival of Adult Rat Islets of Langerhans in Artificial Capillary Culture Units. No date provided.

M. Jensen, Production of Anchorage–Dependent Cells–Problems and Their Possible Solutions, *Biotechnology and Bioengineering*, vol. XXIII, pp. 2703–2716, 1981.

E. Swabb, J. Wei, and P. Gullino, Diffusion and Convection in Normal and Neoplastic Tissues, *Cancer Research*, vol. 34, pp. 2814–2822, Oct. 1974.

M. Turner, M. Londei, and M. Feldmann, Human T Cells From Autoimmune and Normal Individuals can Produce Tumor Necrosis Factor, *Eur. J. Immunol.*, vol. 17, pp. 1807–1814.1987.

A. Foulis, M. McGill, and M. Farquharson, Insulitis in Type 1 (Insulin–Dependent) Diabetes Mellitus in Man–Macrophages, Lymphocytes, and Interferon–Containing Cells, *Journal of Pathology*, vol. 165, pp. 97–103, 1991.

R. Benvenuto, M. Paroli, C. Buttinelli, A. Franco, V. Barnaba, C. Fieschi, and F. Balsano, Tumour Necrosis Factor–Alpha Synthesis by Cerebrospinal–Fluid–Derived T Cell Clones From Patients with Multiple Sclerosis, *Clin. Exp. Immunol.*, vol. 84, pp. 97–102, 1991.

A. Quayle, P. Chomarat, P. Miossec, J. Kjeldsen–Kragh, o. Forre, and J. Natvig, Rheumatoid Inflammatory T–Cell Clones Express Mostly TH 1 But Also TH2 and Mixed (THO–Like) Cytokine Patterns, *Scand. J. Immunol.*, vol. 38, pp. 75–82, 1993.

R. Benvenuto, A. Bachetoni, P. Cinti, F. Sallusto, A. Franco, E. Molajoni, V. Barnaba, F. Balsano, and R. Cortesini, Enhanced Production of Interferon–By T Lymphocytes Cloned From Rejected Kidney Grafts, *Transplantation*, vol. 51, No. 4, pp. 887–890, Apr. 1991.

T. Springer, Adhesion Receptors of the Immune System, *Nature*, vol. 346, pp. 425–434, Aug. 2, 1990.

A. Pierres M. Lopez, C. Cerdan, J. Nunes, D. Olive, and C. Mawas, Triggering CD 28 Molecules Synergize with CD 2 (T 11.1 and T 11.2)–Mediated T Cell Activation, *Eur. J. Immunol.*, vol. 18, pp. 685–690, 1988.

J. Ledbetter, P. Martin, C. Spooner, D. Wofsky, T. Tsu, P. Beatty, and P. Gladstone, Antibodies to Tp67 and Tp44 Augment and Sustain Proliferative Responses of Activated T Cells, *The Journal of Immunology*, vol. 135, No. 4, pp. 2331–2336, Oct. 1985.

P. Vandenberghe, and J. Ceuppens, Immobilized Anti–CD5 Together with Prolonged Activation of Protein Kinase C Induce Interleukin 2–Dependent T Cell Growth: Evidence for Signal Transduction Through CD5, *Eur. J. Immunol.*, vol. 21, pp. 251–259, 1991.

J. Ledbetter, L. Rose, C. Spooner, P. Beatty, P. Martin, and E. Clark, Antibodies to Common Leukocyte Antigen p220 Influence Human T Cell Proliferation by Modifying IL 2 Receptor Expression, *The Journal of Immunology*, vol. 135, No. 3, pp. 1819–1825, Sep. 1985.

R. Van Lier, J. Borst, T. Vroom, H. Klein, P. Van Mourik, W. Zeijlemaker, and C. Melief, Tissue Distribution and Biochemical and Functional Properties of Tp55 (CD27), a Novel T Cell Differentiation Antigen, *The Journal of Immunology*, vol. 139, No. 5, pp. 1589–1596, Sep. 1, 1987.

CELL GROWING DEVICE FOR IN VITRO CELL POPULATION EXPANSION

This application is a continuation of Ser. No. 08/506,173, filed Jul. 26, 1995, now U.S. Pat. No. 5,627,070.

BACKGROUND OF THE INVENTION

The present invention relates to hollow fiber cartridge devices for in vitro cell growth or cell population expansion.

Hollow fiber cartridges or bioreactors for in vitro cell growth are well known in the art and are available from several commercial sources. These devices generally have a housing and a plurality of capillaries or hollow fiber membranes. The capillaries extend between an inflow opening at one end of the cartridge and an outflow opening at the other end. The capillaries have selectively permeable walls through which growth media or culture media, carrying essential nutrients and gases, can diffuse. The interiors of the walls of the plurality of capillaries define a lumen extending between the inflow and outflow openings, and the outside of the capillaries and the housing define an extracapillary space (ECS) where cell growth or population expansion typically takes place. The housing generally includes one or two ports providing access to the ECS so that cells may be added or removed therefrom.

The cells are typically cultured in the ECS in growth media which originates from the lumen. The media in the lumen diffuses through the selectively permeable walls of the hollow fiber membranes into the ECS to stimulate the culture or growth of the cells. To cause media to move through the walls of the hollow fiber membranes into the ECS, growth media is typically pumped through the lumen of the cartridge.

As the media passes from the inflow opening at one end of the cartridge, through the lumen, and out the outflow opening at the other end of the cartridge, a pressure drop occurs from the inflow opening to the outflow opening. At the higher pressure inlet end of the cartridge, a radial convective flow of media moves from the lumen to the ECS bathing the cells in fresh nutrient-containing media. At the opposite end of the cartridge, near the outflow opening, media flows in the opposite direction, thereby removing metabolic waste products and other secreted cell products from the ECS and carrying them through the hollow fiber membranes and into the lumen. These products are then carried out of the cartridge through the outflow opening. Such devices are disclosed by Knazek et al. (U.S. Pat. Nos. 3,821,087; 3,883,393; and 4,220,725) and Yoshida et al. (U.S. Pat. No. 4,391,912).

In recent years, there has been an increasing demand for mammalian cell secreted products. Mammalian cell culture is now utilized to produce many important cell products for human use including monoclonal antibodies, vaccines, lymphokines, hormones, growth factors, enzymes, and other recombinant DNA products. As these products move from research and development, through clinical trials and to the market, a need for an economical large-scale method of production is required. The hollow fiber cell culture devices disclosed by Knazek et al. and Yoshida et al. are not suitable for large-scale manufacturing of mammalian cell secreted products.

These devices are of limited value for large-scale cell production and manufacturing of secreted cell products, particularly mammalian cell products, because of reasons related to the following: (1) the relatively large molecular weight cut-offs of the hollow fiber membranes which allows the required amount of oxygen to enter the ECS, but do not retain all secreted cell products or expensive serum-type nutrients; (2) inefficient oxygen diffusion to the ECS which limits cell growth; (3) formation of nutrient gradients which limit cell growth; and (4) formation of microenvironments for cell growth within the ECS which limits the full use of the entire capacity of the devices for cell growth.

The prior art devices utilize hollow fiber capillary membranes that have large enough molecular weight cut-offs to enable the secreted cell products to pass from the ECS to the lumen. This is undesirable for large-scale production because the secreted cell products become diluted in the large volumes of media necessary to maintain the cells. In addition, serum supplements to the media are generally required on the lumen side of the device. Serum addition to large volumes of media, which are necessary for large-scale production, can be very expensive and can also result in the extensive addition of impurities (e.g. contaminating proteins) to the already significantly diluted secreted cell products. These impurities can increase the cost of purifying the secreted products and often result in decreased yields.

If lower molecular weight cut-off hollow fiber capillaries are utilized in these devices, however, oxygen diffusion to the cells in the ECS will be severely limited. The smaller the cut-off, the less oxygen diffusion. The prior art devices often include a second type of hollow fiber capillary that is especially permeable to nutrients (see e.g. Knazek et al. U.S. Pat. No. Nos. 3,821,087; 3,883,393). This is also undesirable for large-scale production, because cells will preferentially grow on the nutrient source capillaries, not the oxygenation capillaries, thereby decreasing the surface area in the device utilized for cell growth. Furthermore, the inclusion of oxygenation capillaries in those devices, which generally have large molecular weight cut-offs (e.g. about 0.2 microns), does not allow for the retention of secreted cell products or other high molecular weight proteins in the ECS.

It is desirable to retain secreted cell products in the ECS in large-scale production systems, because this allows the secreted cell products to be concentrated in the ECS, rather than being concentrated after leaving the cartridge using one of several tedious or time consuming concentration procedures. It will be appreciated that highly concentrated products are less expensive to process and purify. It is also desirable to retain expensive high molecular weight proteins necessary for cell growth (e.g. serum, growth factors, hormones and cell secreted products) in the ECS. This would allow for the addition of these molecular species in relatively modest quantities to the ECS, rather than to the large lumenal media volume, which would require significantly larger quantities in order to provide the necessary concentrations.

The prior art hollow fiber devices are also limited in their use for large-scale production of secreted cell products by the formation of gradients in the ECS. When nutrient media is delivered via a motive force to the inflow opening of the hollow fiber device, the porous nature of the capillaries causes a change in hydrostatic pressure across the length of the cartridge. Cells at the inlet or high pressure end are continually exposed to a convective flow of fresh nutrients and oxygen, while cells at the outlet or low pressure end are continually exposed to a concentration of metabolic waste products from cells upstream and have limited access to fresh nutrients and oxygen. This results in the formation of a heterogeneous culture environment in the cell-occupied ECS due to the unequal nutrient distribution and the concentration of waste products. These nutrient gradients make it impractical to construct cartridges any longer than about 3-4 inches in length. Longer lengths only provide sufficient nutrients for cell growth in the high pressure inlet portion of the ECS.

Poor circulation of the media in the ECS of prior art devices can also lead to the formation of microenvironments having widely varying cell growth potentials. Microenvironments can occur when pockets of metabolically-active cells near the inlet end of the device secrete waste products into an immediately adjacent area. The waste products accumulate and are not quickly removed through the outlet end of the device. This accumulation of waste products results in microenvironments where cells are unable to grow. It will be appreciated that increasing the length of these devices simply increases the pressure drop and results in a worsening of the problems associated with the gradients and microenvironments created in the prior art devices. These problems severely limit the use to these devices for large-scale production of secreted cell products.

Knazek et al. (U.S. Pat. No. 4,184,922) disclose an improved device that decreases the microenvironment formation problem. This is accomplished by weaving together two separate perfusion circuits. By altering the pressure differences between the circuits, waste products can be removed more efficiently. However, this device still allows for the formation of gradients, which therefore make it unsuitable for large-scale production.

Cracauer et al. (U.S. Pat. No. 4,804,628) disclose an improved hollow fiber culture device that incorporates an external chamber in fluid communication with the ECS. By pressurizing the lumenal flow path, media flux to the ECS is increased. As media is forced into the ECS at the inlet end of the device, it subsequently is forced down the length of the cartridge to the outlet end. A percentage of the media moves into the expansion chamber through a unidirectional valve and a percentage exits across the capillaries to the lumen as in conventional devices. When the external chamber fills, the pressure in the chamber is increased to force the media back into the ECS through a second unidirectional valve which directs the media to the area of the ECS near the inlet end of the cartridge. This cycling helps mix the ECS media, thereby minimizing gradients and microenvironments which might otherwise exist. Oxygen diffusion is still limited, however, and gradients still occur.

The present invention is designed to overcome these and other limitations of the prior art devices and to provide a cell culture environment where cells are equally perfused with nutrients, and waste products are equally removed across the entire length of the hollow fiber cartridge.

SUMMARY OF THE INVENTION

In accordance with the present invention, a cell growing device for in vitro cell population growth is provided wherein the cell growth occurs in fluid growth media within the device. The device comprises a first hollow fiber cartridge having a housing and a plurality of capillaries. Each of the capillaries includes walls having interiors and exteriors. The housing has a first inflow opening and a first outflow opening. The plurality of capillaries extend between the first inflow opening and the second outflow opening and at least one of the capillaries has selectively permeable walls. The interiors of the walls of the plurality of capillaries define a first lumen extending between and being in fluid communication with the first inflow and the first outflow openings. The exteriors of the walls of the plurality of capillaries and the housing define a first ECS. The housing has a first primary orifice in fluid communication with the first ECS.

The device further includes an outflow blocking mechanism for substantially blocking a flow of media from the first lumen via the first outflow opening, wherein the outflow blocking mechanism can be closed to substantially block the flow of media from the first lumen via the first outflow opening such that substantially all of an influx of growth media into the first lumen via the first inflow opening is directed across the capillary walls into the first ECS. Preferably, the outflow blocking mechanism can be alternately opened and closed such that the flow of media from the first lumen via the first outflow opening is alternately permitted and substantially blocked. In preferred embodiments, the outflow blocking mechanism includes a first valve in fluid communication with the first outflow opening distal to the first lumen, wherein the valve can be alternately opened and closed such that the flow of media from the first lumen via the first outflow opening is alternately permitted and substantially blocked. Preferably, the device includes a controlling computer programmed to alternately switch the first valve open and closed.

In a preferred embodiment, a cell growing device for in vitro cell population growth is provided wherein cell growth occurs in fluid growth media within the device. The device comprises first and second hollow fiber cartridges and a fluid connecting mechanism for fluidly connecting the first and second cartridges. Each of the cartridges include a housing and a plurality of capillaries. The housing of the first cartridge including a first inflow opening and a first outflow opening and the housing of the second cartridge including a second inflow opening and a second outflow opening. The plurality of capillaries in each cartridge extend between the respective inflow opening and outflow openings.

At least one of the capillaries of each cartridge includes selectively permeable walls. The interiors of the walls of the plurality of capillaries in each cartridge define a lumen, the first lumen extending between the first inflow and the first outflow openings and the second lumen extending between the second inflow and the second outflow openings. The capillaries and the housing of each cartridge define an ECS, the first ECS being in the first cartridge and the second ECS being in the second cartridge. The housing of each cartridge includes a primary orifice in fluid communication with the ECS of each cartridge, the first primary orifice being in fluid communication with the first ECS and the second primary orifice being in fluid communication with the second ECS. The fluid connecting mechanism include a recirculation mechanism for recirculating fluid media from the outflow openings of the respective hollow fiber cartridges to inflow openings thereof and an extracapillary connecting mechanism for fluidly connecting the first ECS with the second ECS, wherein all fluid communication between the first cartridge and the second cartridge prior to passing through the recirculation mechanism passing through the extracapillary connecting mechanism.

Nutrient media is delivered to the lumen of the first cartridge via the first inflow opening by a motive force. The lumenal flow path is blocked after the first outflow opening, forcing all the media to ultrafiltrate across the capillaries to the ECS. The first primary orifice is fluidly connected to the second primary orifice. Therefore, the media moves through the first primary orifice and enters the second ECS through the second primary orifice. The media then moves across, or ultrafiltrates across, the capillary membranes into the second lumenal space and flows out the second outflow opening.

Cells can be placed in the first ECS and retained in the first cartridge by placing a cell filter, preferably a microporous filter, after the first primary orifice. In this manner, all of the cells in the ECS of the first cartridge are continually perfused with fresh nutrients and oxygen from the ultrafiltrative flow from the lumen. Metabolic waste products are removed by filtration across the capillaries in the second cartridge. Alternately, cells can be placed in the ECS of each cartridge and the direction of media flow reversed at preset intervals. When cells are placed in the ECS of both cartridges, a second cell filter is placed on the second primary orifice to retain cells in the ECS of the second cartridge.

In alternate preferred embodiments, the extracapillary connecting mechanism includes a connecting chamber in fluid communication with the first and second primary orifices. The connecting chamber preferably includes a monitoring mechanism for monitoring the presence of oxygen gas ($O_2$) and hydrogen ion concentration (pH), a gas transfer mechanism for exchanging gas across a membrane separating the media from a controlled gaseous environment within the gas transfer mechanism, and a gas delivery mechanism for delivering specific gases such as oxygen gas ($O_2$), carbon dioxide ($CO_2$) and nitrogen gas ($N_2$) to the controlled gaseous environment.

The cell growing device preferably includes an outflow valve mechanism for alternatively preventing the flow of media from exiting via the first or second outflow opening respectively, an inflow valve mechanism for alternately directing media into the lumen of the first or second hollow fiber cartridge via the first or second inflow opening, respectively, and a control mechanism for controlling the inflow and outflow valve mechanism such that the flow of media alternately passes either into the first lumen via the first inflow opening or into the second lumen via the second inflow opening. In either event, the flow of media subsequently passes through the capillary walls of the capillaries of the respective cartridge and into the respective ECS, through the connecting mechanism, into the ECS of the other cartridge, through the capillary walls of the capillaries the other cartridge, into the lumen and out through the outflow opening of the other cartridge. Preferably, the control mechanism include a controlling computer.

In a preferred embodiment, the cell growing device includes a plurality of first cartridges and a plurality of second cartridges, wherein the first cartridges are connected in parallel with the fluid connecting mechanism and the second cartridges are connected in parallel with the fluid connecting mechanism. In other preferred embodiments, the device includes a flow monitoring and restricting mechanism for individually monitoring and adjusting media flow to each of the hollow fiber cartridges via the respective inflow openings and via the respective primary orifices such that the respective flow of media therethrough into the respective lumen or ECS of each of the cartridges can be monitored and adjusted to maintain equal flow to each cartridge under conditions of changing resistance to media flow.

The present invention also provides methods for culturing cells in vitro in a cell growing device. One of these methods provides for culturing cells in vitro in a cell growing device wherein nutrient gradients along the length of hollow fiber membranes of a first hollow fiber cartridge of the cell growing device are minimized when fluid media is pumped into the cartridge. The method comprises the steps of culturing cells in the cell growing device wherein the device includes a media flow limitation mechanism for substantially stopping the flow of media out of the lumen via the outflow opening of the first cartridge; and substantially stopping the flow of media out of the first lumen via the outflow opening with the media flow limitation mechanism such that substantially all media flowing out of the first lumen flows into the first ECS.

An alternate method for culturing cells in vitro in a cell growing device including first and second hollow fiber cartridges and connecting mechanism for fluidly connecting the first and second cartridges comprises the steps of alternately circulating media through each of individual first and second hollow fiber cartridges via each respective inflow opening in order to provide growth media for culturing cells in the device; and alternately substantially stopping the flow of media out of the lumen of each respective hollow fiber cartridge via each respective outflow opening with media flow limitation mechanism when media is circulated into each cartridge via its respective inflow opening such that substantially all media flowing out of the lumen out of respective cartridge flows into the ECS of the cartridge and out of the cartridge via a connecting mechanism connecting each first ECS with each second ECS such that fluid can communicate therebetween.

Another alternate embodiment provides a method for culturing cells in vitro in a cell growing device comprising the steps of growing and maintaining cells in an ECS of a first hollow fiber cartridge; directing the flow of media across the capillary walls from the lumen into the ECS of the cartridge wherein substantially all of the media flows from the lumen to the ECS and substantially all of the media flowing through the lumen and out of the cartridge via the outflow opening is blocked; and subsequently redirecting the flow of media across the capillary walls from the ECS into the lumen of the cartridge wherein the cell growing device includes a mechanism for monitoring and adjusting the pH of the media in the device, and wherein the pH of the media is monitored and adjusted before the media permeates across the capillary walls into the lumen. Alternately, the cell growing device includes a mechanism for monitoring and adjusting the oxygen concentration of the media in the device. Preferably, the device includes a mechanism for monitoring and adjusting both the oxygen concentration and the pH of the media in the device.

Another method in accordance with the present invention comprises the steps of growing and maintaining cells in a cell growing device including first and second hollow fiber cartridge, and alternately directing the flow of media, first, from the lumen of the first cartridge, across the capillary walls and into the ECS thereof, and into the ECS of the second cartridge, and across the capillary walls into the lumen thereof, and, second, from the lumen of the second cartridge, across the capillary walls into the ECS thereof, and into the ECS of the first cartridge, and across the capillary walls and into the lumen thereof, wherein alternating the direction of the flow of media reverses the flow of media from one of the cartridge to the other. Preferably, the method further comprises the step of monitoring and adjusting the oxygen concentration of the media in fluid communication with the ECS of either cartridge or alternately monitoring and adjusting the pH of the media. Preferably, both the oxygen concentration and the pH of the media are monitored and adjusted and the method further comprises the step of substantially stopping the flow of media out of the lumen of either cartridge when the flow of media from the lumen of the respective cartridge is directed across the capillary walls and into the ECS thereof, wherein the device includes a valve mechanism for alternately substantially blocking the flow of media from the lumen of either cartridge via each respective out flow opening.

The present invention provides many advantages over the prior art. Because the growth media pumped into any cartridge via an inflow opening cannot flow out of the lumen of the cartridge via the outflow opening, and must instead ultrafiltrate across the hollow fiber membranes to leave the lumen, the nutrient gradients along the length of the entire hollow fiber membranes are substantially eliminated or significantly reduced. This permits consistent diffusion of nutrients to all cells along the entire length of the hollow fiber membranes. This, in turn, allows for consistent maximizations of cell growing potential along the entire length of the cartridge, thereby providing an advantage over the prior art.

Equal perfusion of nutrients across the entire length of the cartridge, enables larger cartridges to be utilized for the large-scale production of secreted cell products. Perfusion of nutrients by ultrafiltration has been shown to be most desirable for promoting cell growth. Small molecular weight cut-off fibers can also be utilized in the present invention to retain secreted products and other expensive growth factors in the ECS. The monitoring mechanism for oxygen and pH, combined with the controlled gas transfer mechanism provides a consistent homogenous environment for the cells and overcomes the resistance of the capillaries to diffusion of oxygen from the lumen to the ECS. This is because oxygen can be added to the ECS side of the cartridge and does not have to diffuse to the ECS from the lumen.

The above-described features and advantages, along with various other advantages and features of novelty, are pointed out with particularity in the claims of the present application. However, for a better understanding of the invention, its advantages, and objects obtained by its use, reference should be made to the drawings, which form a further part of the present application, and to the accompanying descriptive material in which there is illustrated and described preferred embodiments of the present invention.

DETAILED DESCRIPTION OF THE PREFERRED EMBODIMENTS

Figures 1, 2, 3:
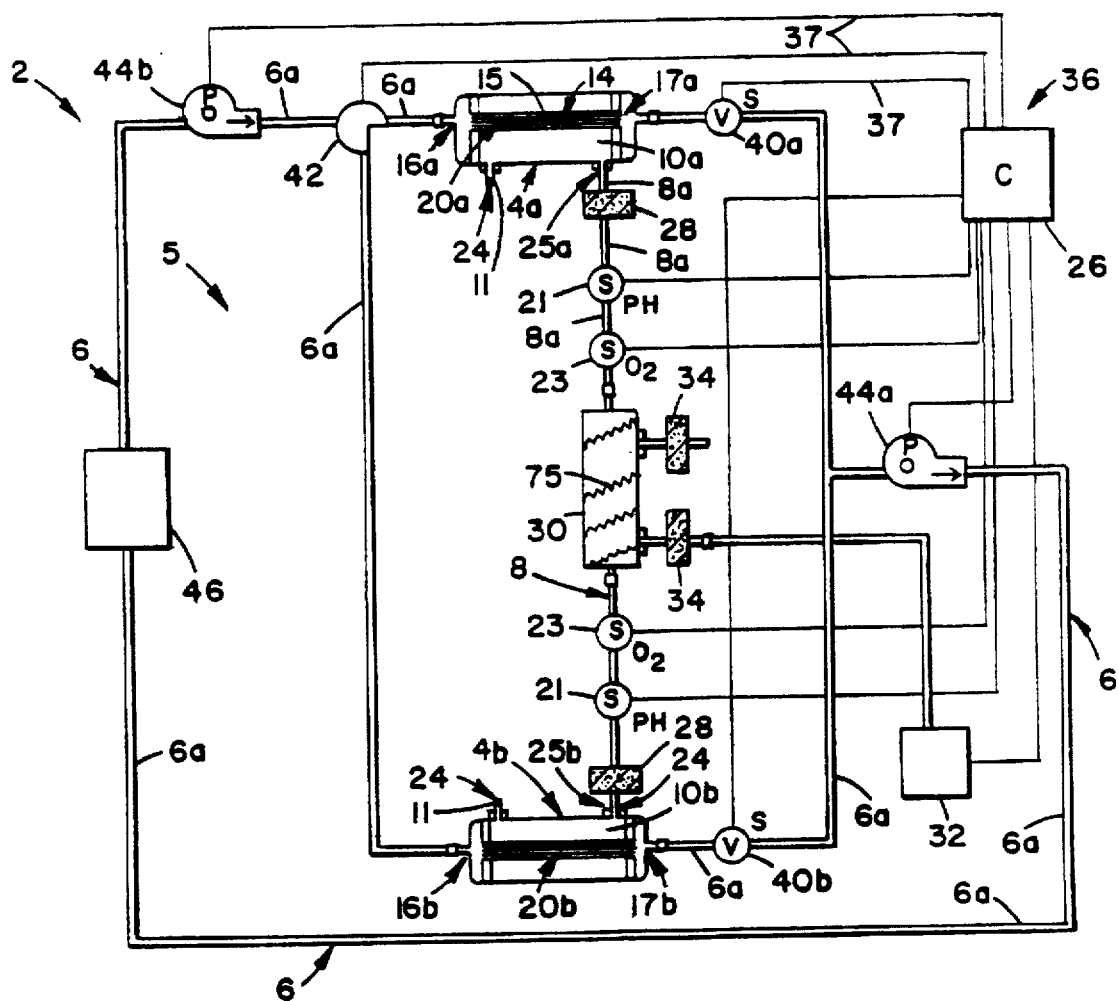
FIG. 1 is a schematic diagram of a cell growing device in accordance with the present invention having individual first and second hollow fiber cartridges.
FIG. 2 is a longitudinal cross-sectional view of the hollow fiber cartridge shown in FIG. 1.
FIG. 3 is a cross-sectional view at line 3—3 of the cell growing device shown in FIG. 2.

Referring now to the drawings, and specifically to FIGS. 1, 2 and 3, FIG. 1 shows a schematic diagram of the fluid pathways of an automated cell growth device 2 in accordance with the present invention. The device 2 includes individual first and second hollow fiber cartridges 4a and 4b which are fluidly connected by a fluid connecting mechanism 5.

The hollow fiber bioreactor or cartridge 4 shown in FIG. 2 is the same as the first and second cartridges 4a and 4b shown in FIG. 1. Each cartridge 4 has a housing 12 and a plurality of capillaries 14. Each of the capillaries 14 has walls 15 having interior 15a and exteriors 15b (see FIG. 3). The housing 12 has an inflow opening 16 at one end and an outflow opening 17 at the other end. The plurality of capillaries 14 extend between the inflow opening 16 and the outflow opening 17. Each of the capillaries 14 preferably have selectively permeable walls 15. The interiors 15a of the walls 15 of the plurality of capillaries 14 in each cartridge 4 define a lumen 20 extending between and fluidly communicating with the inflow and outflow openings 16 and 17. The exteriors 15b of the capillaries 14 and the housing 12, preferably including potting material 18 which binds the capillaries 14, define an ECS 10 where cell growth or cell population expansion takes place. A cross-sectional view of the cartridge 4 shown in FIG. 2 is shown in FIG. 3.

The housing 12 includes the potting material or integral disk portions 18 at each end which extend circumferentially around and thereby receive the plurality of capillaries 14 which are bundled together. The disks 18 separate the respective inflow and outflow openings 16 and 17 from the ECS 10. Each cartridge 4 has two cartridge ports 24 that provide for fluid communication with the ECS 10 extends circumferentially around the plurality of capillaries 14, which are bundled together toward the center of the cartridge 4. Populations of cells 22 can be transferred into the ECS 10 via either of the cartridge ports 24. It will be understood that such a transfer is preferably done under sterile or aseptic conditions. The ports 24 can be reversibly sealed by a septum 11 to prevent contaminating material from entering the ECS 10 through the ports 24. The cells 22 are injected through the septum 11 with a syringe.

Figure 4:
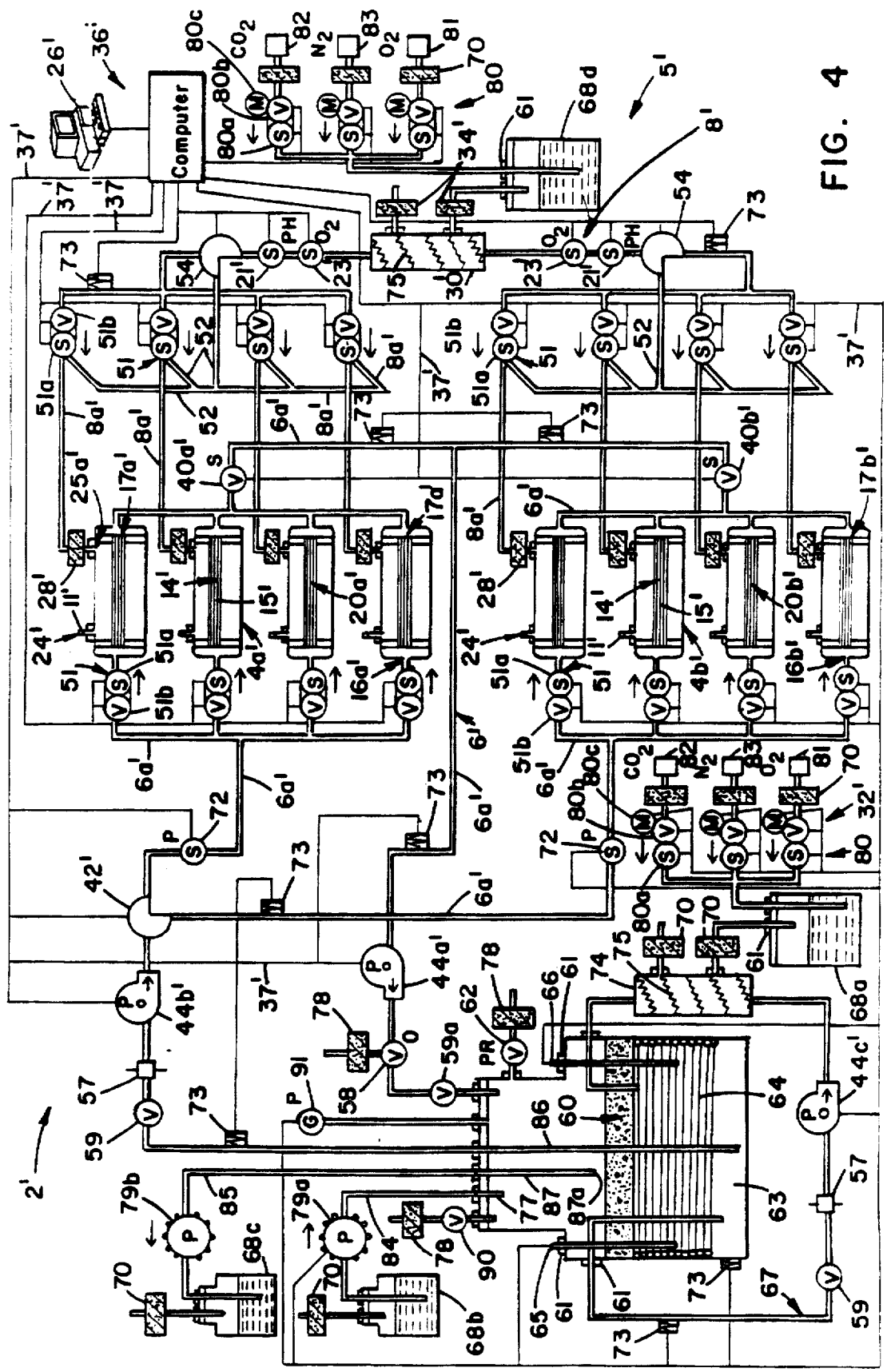
FIG. 4 is a schematic diagram of a cell growing device in accordance with the present invention having pluralities of first and second hollow fiber cartridges.

Referring now also to FIG. 4, which shows a schematic diagram of a preferred cell growing device 2', which has four of each of the first and second hollow fiber cartridges 4a' and 4b'. The plurality of first cartridges 4a' is connected to the plurality of second cartridges 4b' in a manner which is very similar to a manner in which the first and second cartridges 4a and 4b are connected in the smaller device 2 shown in FIG. 1, except that the individual cartridges 4a' and 4b' in each plurality of cartridges are connected to other portions of the device 2' in parallel.

The fluid connection mechanism 5 shown in FIG. 1 includes a recirculation mechanism 6 and an ECS connecting mechanism 8. The ECS connecting mechanism 8 provides for fluid communication between the ECS 10a of the first cartridge 4a and the ECS 10b of the second cartridge 4b. The ECS connection mechanism 8 connects the cartridges 4a and 4b via cartridge ports 24 on each cartridge 4a and 4b, thereby providing a primary orifice 25a and 25b for fluid communication with the ECS 10a and 10b of each cartridge 4a and 4b. The primary orifice 25a of the first cartridge 4a is connected to the primary orifice 25b of the second cartridge 4b by ECS.

Connectors 8a made of 316 stainless connection tubing. The ECS connectors 8a are interspersed by high molecular weight cut off filters 28 which are used to retain the cells 22 in the ECS 10a and 10b of each respective cartridge 4a and 4b. The ECS connecting mechanism includes in-line sensors 21 and 23 for monitoring hydrogen ion concentration (pH)

and oxygen gas ($O_2$) respectively, and a gas transfer cartridge 30 for exchanging gas across a membrane (not shown) separating growth media from a controlled gaseous environment within the gas cartridge 30. The gas transfer cartridge 30 receives gas through a sterilization filter 34 from a gas delivery mechanism 32 which can deliver adjustable percentages of $CO_2$, $N_2$, and $O_2$ to the controlled environment.

After the growth media flow through the filter 28 from the ECS 10, it flows through the in-line sensors 21 and 23 for pH and $O_2$, respectively. The in-line sensors 21 and 23 are connected to a computer control mechanism 36, including a computer 26, and transmit information which the computer 26 interprets. In response, the computer control mechanism 36 subsequently adjusts the relative concentrations of oxygen gas ($O_2$), carbon dioxide ($CO_2$) and nitrogen gas ($N_2$) which are delivered to the gas transfer cartridge 30 by the gas delivery mechanism 32.

The device 2 is automated such that the computer control mechanism 36 is capable of alternating the direction of the flow of media through the ECS connecting mechanism 8. In this way, the cells growing in the ECS 10 of each of the cartridges 4a and 4b will be alternately supplied with growth media from the ECS connecting mechanism 8 after the pH has been adjusted and the oxygen concentration has been replenished, thereby enhancing the growth potential of the cells.

The computer 26 is part of the computer control mechanism 36 that includes all of the computer connections 37 between the computer 26 and the various elements of the device 2 which are computer controlled. In order to vary the direction of the flow of media through the ECS connecting mechanism 8, the computer control mechanism 36 switches, opens or closes various valves in the recirculation mechanism 6.

The recirculation mechanism 6 includes recirculation connectors 6a that provide fluid pathways which interconnect the outflow openings 17a and 17b of cartridges 4a and 4b to the inflow openings 16a and 16b of the same cartridges 4a and 4b. The recirculation connectors 6a are made of 316 stainless steel tubing. Also included in the recirculation mechanism are two solenoid valves 40a and 40b adjacent and proximate to the outflow openings 17a and 17b respectively, of the respective cartridges 4a and 4b. The solenoid valves 40a and 40b substantially stop the flow of media from the respective cartridge lumens 20a and 20b through the respective outflow opening 17a and 17b when they are closed. This forces any fluid media flowing into the lumen 20 through an inflow opening 16 to ultrafiltrate across the capillary walls 15 of the capillaries 14 and into the ECS 10 when the solenoid valve 40a or 40b for one cartridge 4a or 4b or the other is closed. The solenoid valves 40a and 40b are connected to the computer control mechanism 36. The control mechanism 36 is programmed so that the solenoid valves 40a and 40b, alternately opened or closed such that when one is open the other will be closed.

At the same time that the solenoid valves 40a and 40b are individually opened and closed, the control mechanism 36 simultaneously switches a three-way valve 42 controlling the flow of media into the respective cartridges 4a and 4b through their respective inflow openings 16a and 16b such that the flow of media will be directed to one cartridge 4a or 4b or the other at any particular moment. The switching of the three-way valve 42 and the solenoid valves 40a and 40b is coordinated such that when the flow of media is directed the inflow opening 16a of the first cartridge 4a, the solenoid valve 40a is closed to prevent the flow of media from the lumen 20a from passing through the outflow opening 16a, while the solenoid valve 40b is open, thereby allowing the flow of media from the lumen 20b to pass through the outflow opening 17b of the second cartridge 4b.

Alternately, when the three-way valve directs the flow of media through the inflow opening 16b of the second cartridge 4b, the solenoid valve 40b is closed and the solenoid valve 40a is open. In this way, the control mechanism 36 directs the flow of growth media through the inflow opening 16a or 16b of one cartridge 4a or 4b and out of the outflow opening 17a or 17b of the other, thereby forcing the media to pass through the capillary walls 15 of both cartridges 4a and 4b before the media is recirculated back to the inflow opening 16a or 16b of either cartridge 4a or 4b via the recirculation mechanism 6.

Because the two solenoid valves 40a and 40b are switched from open to closed and from closed to open simultaneously, the flow of media into the recirculation mechanism 6 can only pass into the recirculation mechanism 6 through the outflow opening 17a or 17b of one or the other of the cartridges 4a or 4b at any one moment in time. As one solenoid valve 40a or 40b is closing, the other is opening and the three-way value 42 is switching so as to redirect the flow of recirculated growth media from one inflow opening 16a or 16b to the other. As this switching takes place the direction of the flow of media within the ECS connecting mechanism 8 is also switched.

The recirculation mechanism 6 includes the recirculation connectors 6a that connect the respective inflow and outflow openings 16 and 17 of the cartridges 4a and 4b. The recirculation connectors 6a from the outflow openings 17a and 17b join just before reaching a centrifugal pump 44a, to form a single stainless steel pathway which carries the recirculated media to the three-way valve 42. The centrifugal pump 44a pumps the media through a regeneration mechanism 46 having similar functions to those found in the ECS connecting mechanism 8 wherein the media is replenished with nutrients and essential gases, and waste products from cell growth are preferably removed. The oxygen gas ($O_2$) and hydrogen ion concentration (pH) are monitored and adjusted in the regeneration mechanism 46 as previously described in relation to the ECS connecting mechanism 8. After the media is regenerated in the regeneration mechanism 46, the media then flows through a second centrifugal pump 44b to the three-way valve 42, where it is directed to the inflow opening 16a or 16b of one or the other hollow fiber cartridge 4a or 4b.

The hollow fiber bioreactors or cartridges 4 are preferably commercially available hollow fiber dialysis cartridges available from CD-Medical, Inc. of Hialeah, Fla. It will be appreciated, however, that any hollow fiber bioreactors may be used whether commercially available or not. Preferably, the cartridge 4 will have a molecular weight cut-off (MWC) of about 50,000 daltons, more preferably about 30,000 daltons, even more preferably about 15,000 daltons, and most preferably about 10,000 daltons. A preferred cartridge having a 30,000 dalton MWC, is the CELL-PHARM BR 130. The most preferred cartridge, which has a 10,000 dalton MWC, is the CELL-PHARM BR 110 or the CELL-PHARM Model I from CD-Medical, Inc. of Hialeah, Fla.

The in-line sensors 21 and 23 include a pH electrode and an oxygen ($O_2$) electrode respectively. The information from the pH electrode and the $O_2$ electrode is interpreted by the computer control mechanism 36 and utilized to adjust the mixture of $O_2$, $N_2$ and $CO_2$ delivered to the gas transfer cartridge 30 by the gas delivery mechanism 32. Similar functions are effected by similar elements in the regeneration mechanism 46. The media directed toward the cartridge 30 and away from the cartridge 30 is monitored by these in-line sensors 21 and 23 in the fluid pathway. The ability to reverse the flow of media passing through the ECS connecting mechanism 8, and the ability to adjust the pH and oxygen levels therein, among other things, enhance nutrient perfusion and oxygen delivery so that a cell population of about $1 \times 10^9$, preferably between approximately $5 \times 10^9$ and $10 \times 10^9$ cells can be supported in each cartridge 4, and between approximately $5 \times 10^9$ and $10 \times 10^9$, preferably between approximately $4 \times 10^{10}$ and $10 \times 10^{10}$ cells can be supported by the preferred device shown in FIG. 4.

Referring now also to FIG. 4, the automated cell growth device 2' shown in FIG. 4 has similar fluid dynamics to that of the less complicated device 2 shown in FIG. 1. The plurality of first hollow fiber cartridges 4a' are connected in parallel with one another as are the plurality of second hollow fiber cartridges 4b'. Like the simpler service 2 shown in FIG. 1, the outflow openings 16' are connected to a recirculation mechanism 6'. The flow of media from the lumens 20' through the outflow openings 16' of either group of parallel cartridges 4a' and 4b' are controlled by solenoid valves 40a' and 40b' respectively, which are, in turn, connected to and controlled by the computer control mechanism 36'. The fluid dynamics of the industrial scale cell growing device 2' are controlled by the control mechanism 36' in a manner similar to or parallel to the way they are controlled in the smaller device 2 shown in FIG. 1. The computer 26' is connected to solenoid valves 40a' and 40b' and the three-way valve 42' which each correspond to similar elements of the simpler device 2.

The biggest difference in the industrial scale device 2', as compared to the smaller device 2, is the fact that a plurality of cartridges 4' are connected to the system in parallel in place of the single cartridges 4a and 4b. The flow of media from the lumens 20' through the outflow openings 16' can be alternately stopped by the control mechanism 36' by alternately closing one or the other solenoid valve 40a' and 40b'. Similarly, the three-way valve 42', which is also controlled by the computer control mechanism 36', can be switched to alternate the flow of media directed to the inflow openings 16a' and 16b' of one group of parallel cartridges 4a' or 4b' or the other.

The fluid connecting mechanism 5' of the industrial scale cell growing device 2' includes the recirculation mechanism 6' and the ECS connecting mechanism 8' that each have functions which are equivalent to the corresponding mechanisms 6 and 8 in the smaller device 2. The cells 22' are retained in the ECS 10' by a filter 28' that allows the media to pass out of the primary orifice 25' at a relatively high flow rate. The filter 28' can be any device which allows fluids to pass, but retains cells (e.g. a 5.0 micron filter, large molecular weight cut-off microporous cartridge, or the like). Because there are a plurality of first cartridges 4a' and a plurality of second cartridges 4b', however, each group of which are connected in parallel with the other members of that group, a flow monitoring and restricting mechanism 51 for individually monitoring and adjusting media flow to each of the cartridges 4' via either the respective inflow openings 16' or the respective primary orifices 25' are provided. The flow monitoring and restricting mechanisms 51 include a flow meter or sensor 51a to measure the media flow rate through the fluid path and a needle valve 51b which are connected to the control mechanism 36' are preferably adjusted in response to the information registered on the flow meter 51a. Alternately, the needle valve 51b may be adjusted manually.

Because the needle valve 51b only allows flow in one direction and is only used to monitor and adjust the flow into the cartridges, the ECS connecting mechanism 8' of the industrial scale device 2' is somewhat more complex than the corresponding mechanism 8 of the smaller device 2. Media flow leaving the ECS 10' of the first cartridges 4a' does not pass through the flow monitoring and restricting mechanisms 51. Instead, when media leaves the ECS 10' through the ECS connectors 8a', it is shunted to a bypass pathway 52 in the ECS connecting mechanism 8' when the media reaches the flow monitoring and restricting mechanisms 51. The bypass pathway 52 is connected with an ECS three-way valve 54 that is switched simultaneously with the recirculation three-way valve 42', and the solenoid valves 40a and 40b by the computer control mechanism 36'.

The industrial scale device 2' includes a growth media reservoir 63 that is preferably a 10 liter tank constructed from 316 stainless steel. The tank 63 is wrapped with resistance coils 64 that can generate heat to raise the media temperature above the ambient temperature which is preferably below 37° C. during cell culture operations. Temperature monitoring mechanisms 73 are attached to the stainless steel connecting tubes or connectors 8a' and 6a' at various points, and also to the reservoir 63, to ensure that a proper temperature is reached during an in-line sterilization procedure discussed hereinbelow.

The hydrogen ion concentration (pH) and oxygen ($O_2$) concentration of the growth media in the reservoir 63 is monitored by a pH electrode 65 and an oxygen electrode 66 that are inserted into the reservoir through ports 61 in the reservoir 63. The oxygen concentration ($O_2$) and hydrogen ion concentration (pH) in the growth media 60 in the reservoir 63 is constantly adjusted by circulating the media 60 through a high speed secondary circulation loop 67. The media 60 leaves the reservoir 63 under the motive force of a centrifugal pump 44c' is primed by closing an in-line valve 59 and using a syringe to inject media into the loop 67 through an in-line port 57 located between the valve 59 and pump 44c' in the secondary loop 67. The loop 67 includes a gas transfer cartridge 74 which is preferably identical to the gas cartridge 30' in the ECS connecting mechanism 8'.

The gas delivery mechanism 32' is connected to the computer control mechanism 36', as are the probes 65 and 66 and the pump 44c'. In response to the information regarding pH and oxygen concentration received by the computer 26' from the respective probes 65 and 66, the speed of the pump 44c' and the mixture of gases delivered to the gas cartridge 74 by the gas delivery mechanism 32' are adjusted. Alternately, pump 44c' can be adjusted manually so that the media is pumped at a rate of up to about 400 ml/min or greater. In that event, information regarding the flow rate through the gas transfer cartridge 74 is taken into account during programming of the computer control mechanism 36'. The computer control mechanism 36' controls the mixture of gas leaving the gas delivery mechanism 32' by simultaneously controlling the flow of gas to the gas cartridge 74 from three gas supply reservoirs 81, 82 and 83, which supply oxygen gas ($O_2$), carbon dioxide ($CO_2$) and nitrogen gas ($N_2$), respectively.

The gas flow from each reservoir 81, 82 and 83 is monitored and adjusted by a flow monitoring and adjusting mechanism 80 which includes a flow meter or sensor 80a, a variable adjustment valve 80b, and a stepper motor 80c. All of these elements are connected to the computer control mechanism 36' which integrates the information received therefrom, and adjusts the stepper motors 80c to adjust the valves 80b so that a proper mixture of gas is delivered to the gas cartridge 74. The gas from the reservoirs 81, 82 and 83 is mixed into a common passageway after being passed through a 0.2 micron sterilization filter 70, and then bubbled through aqueous media in a reservoir 68a to humidify the gas. The gas is then passed through a second sterilization filter 70 and into the gas cartridge 74. The gas can leave the cartridge 74 through a second sterilization filter 70. Each of the gas cartridges 30, 30' and 74 have heating elements 75 that allow the temperature in each gas cartridge 30, 30' or 75 to be raised above the ambient temperature. It will be appreciated that any gas transfer cartridge may be used, whether commercially available or not, so long as it meets the needs of the present invention. A preferred gas transfer cartridge, however, is the CELL-PHARM Hollow Fiber Oxygenator, which can be obtained from CD-Medical, Inc., Hialeah, Fla.

After the pH and the oxygen concentration levels of the media 60 are adjusted in the gas transfer cartridge 74, the media is returned to the reservoir 63. In addition to providing an efficient system to control pH and oxygen concentration ($O_2$), the secondary circulation loop 67 also serves to keep the media 60 circulating within the reservoir 63. The gas delivery mechanism 32' in the secondary circulation loop 67 is substantially the same as the gas delivery system 32' in the ECS connecting mechanism 8'. Preferably, the regeneration mechanism 46 in the less complicated cell growing device 2 shown in FIG. 1, also has a gas delivery system that is similar or identical to the system provided by the industrial scale cell growing device 2'.

Fresh media is slowly added to the growth media 60 in the growth media reservoir 63 from a fresh media reservoir 68b. The fresh media is drawn out of the reservoir 68b through a first flexible tube 84 that is connected to a first rigid tube 77 which extends into the media reservoir 63. The flexible tube 84 passes through a first peristaltic pump 79a that pumps the fresh media from the fresh media reservoir 68b into the growth media reservoir 63 at a variable rate. As the fresh media leaves the reservoir 68b, air is drawn into the reservoir 68b through a 0.2 micron sterilization filter 70. At the same time, a second flexible tube 85 that is connected to a second rigid tube 87 which extends into the media reservoir 63, withdraws growth media 60 when the level of the media 60 in the reservoir 63 reaches a height equal to or greater than the lower end 87a of the second rigid tube 87. The media 60 is withdrawn under the motive force of a second peristaltic pump 79b and is delivered into a spent media reservoir 68c. The reservoir 68c is equipped with a sterilization filter 70 that allows gas to escape as the reservoir 68c is filled with media removed from the growth media reservoir 63. In this way, the media is constantly replenished with fresh media, thereby removing waste products and replenishing the nutrients needed for continued cell growth.

Media is withdrawn from the media reservoir 63 to supply the cartridges 4' through a stainless steel tube 86 under the motive force of a centrifugal pump 44b'. This pump 44b' is primed in the same manner as the centrifugal pump 44c' in the secondary circulation loop 67. A three-way valve 42' then directs the growth media alternately to a band of first hollow fiber cartridges 4a' or a bank of second hollow fiber cartridges 4b' via their respective inflow openings 16a' and 16b'.

Figure 5:
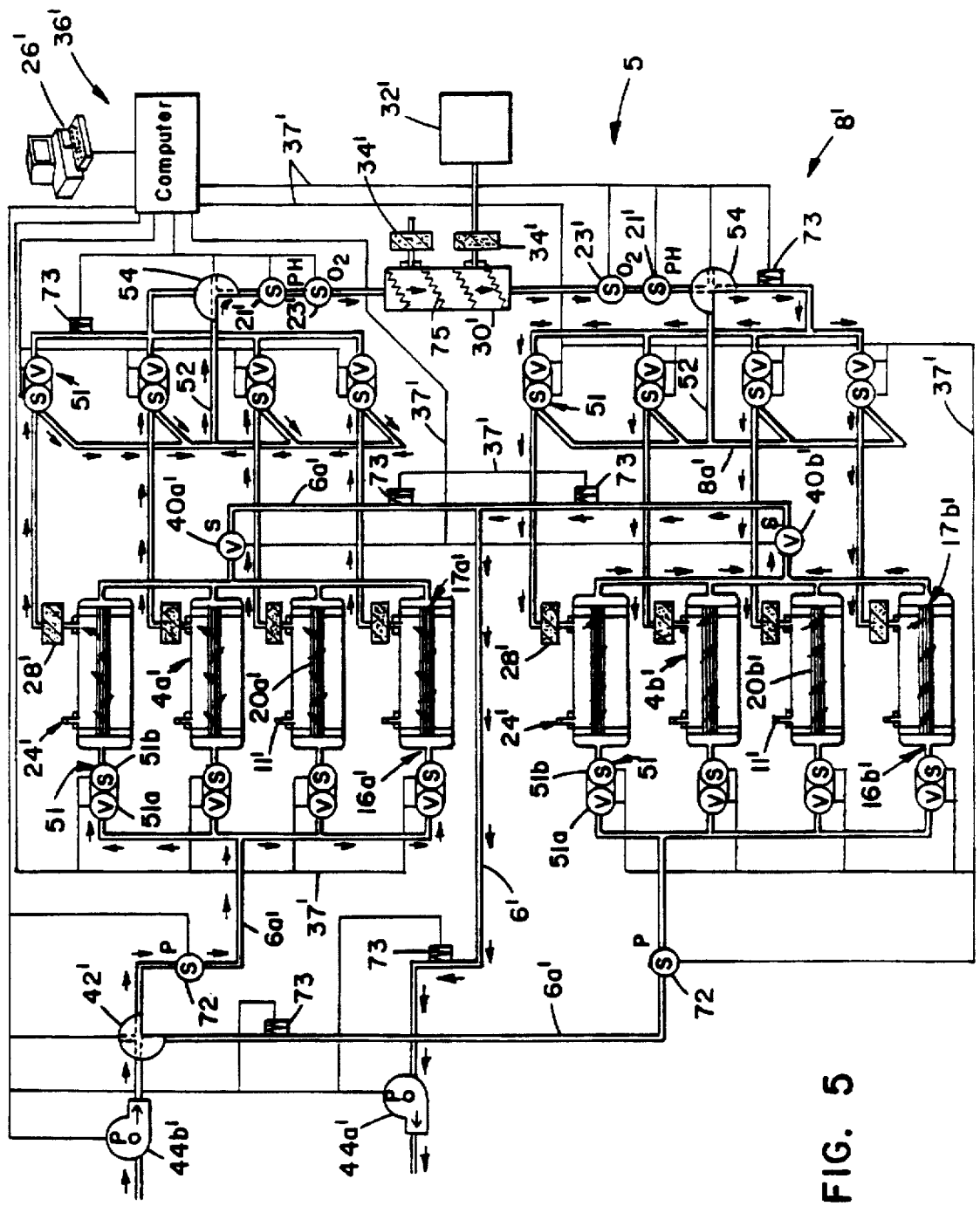
FIG. 5 is a schematic diagram of a portion of the device shown in FIG. 4, wherein arrows illustrate an alternate pathway for the flow of growth media through the cartridges and their connectors.
Figure 6:
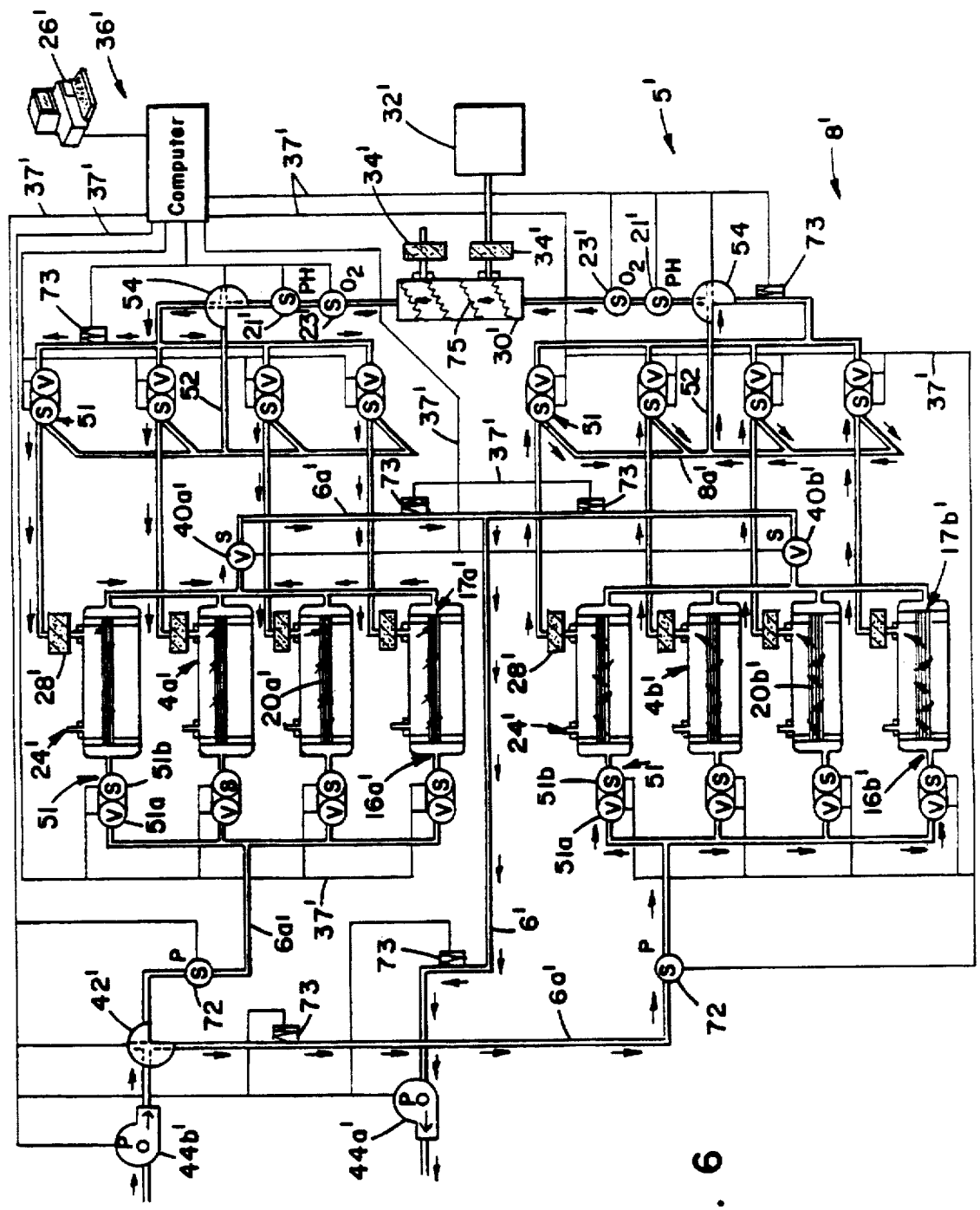
FIG. 6 is a schematic diagram of a portion of the device shown in FIG. 4, wherein arrows illustrate another alternate pathway for the flow of growth media through the cartridges and their connectors.
Figure 7:
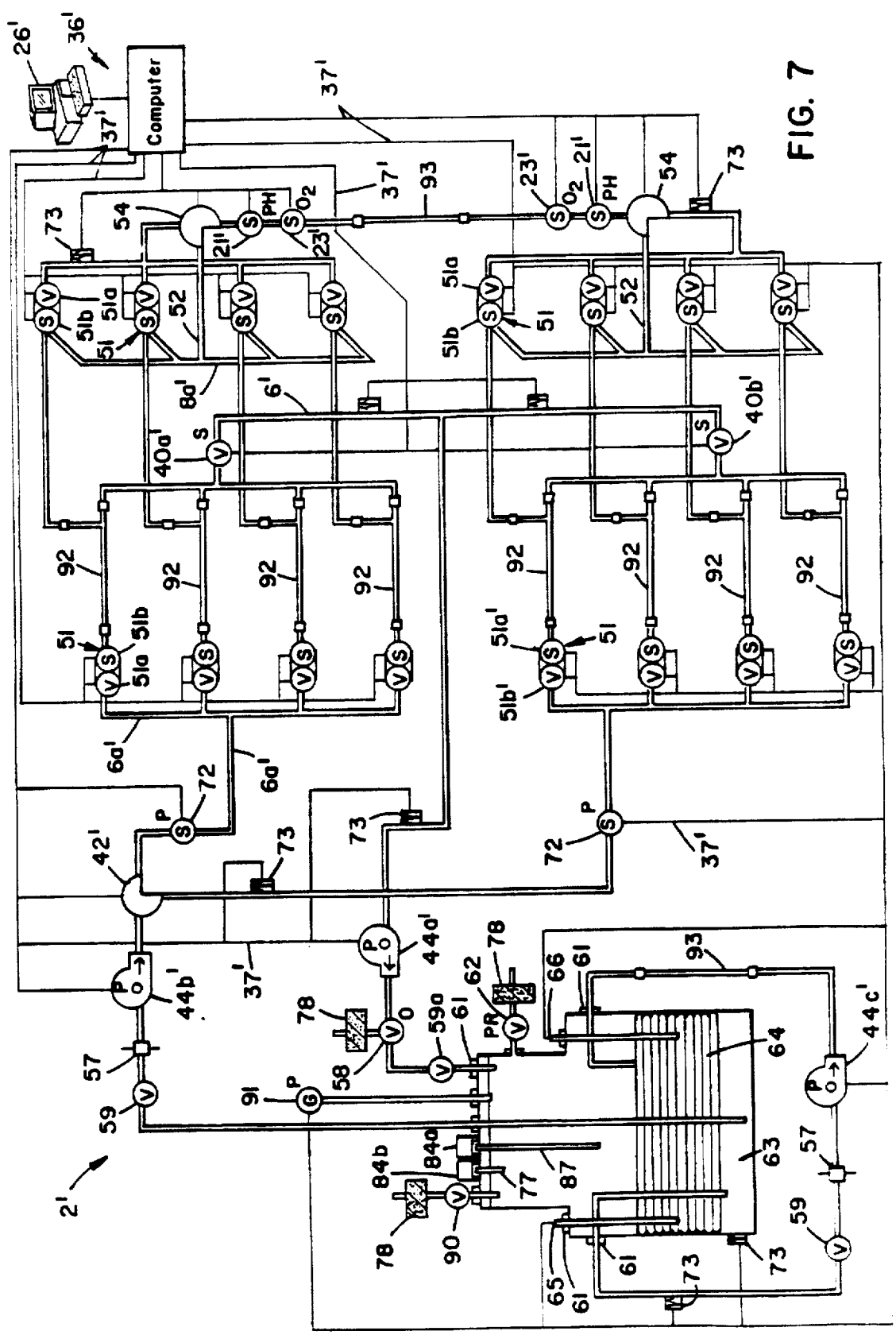
FIG. 7 is a schematic diagram of a modification of the cell growing device shown in FIG. 4 after portions of the device have been removed and connectors and caps have been attached so that the fluid pathways in the device may be heat sterilized.

Referring now also to FIGS. 5 and 6, the growth media passing through the three-way valve 42' will follow two alternate pathways. When the three-way valve 42' directs the growth media to the inflow openings 16a' of the plurality of first hollow fiber cartridges 4a', the fluid path will follow the path delineated by the arrows shown in FIG. 5. In such a case, the solenoid valve 40a' is closed, preventing the flow of media from the lumen 20a' of the plurality of first cartridges 4a'. When the solenoid valve 40a' is closed, the solenoid valve 40b' is open so that media can flow from the lumens 20b' of the plurality of second cartridges 4b' through their respective outflow openings 17b' and into the recirculation mechanism 6'. In such a case, the flow of media in the ECS connecting mechanism 8' is directed from the ECS 10a' of the first cartridges 4a' to ECS 10b' of the second cartridges 4b'.

When the flow of media through the three-way valve 42' is directed through the inflow opening 16b' of the plurality of second hollow fiber cartridges 4b', the direction of the media flow in the ECS connecting mechanism 8' is reversed as is shown in FIG. 6. In that situation, the solenoid valve 40b' is closed and the solenoid valve 40a' is open so that the media may enter the recirculation mechanism 6' after it passes out of the lumens 20a' of the first cartridges 4a' through the outflow openings 17a' thereof.

Media entering either the plurality of first or second hollow fiber cartridges 4a' or 4b', which each contain four cartridges 4' in the preferred embodiment, is split into four fluid flow paths which flow through a flow monitoring and restricting mechanism 51 prior to entering each respective cartridge 4'. Each flow monitoring and restricting mechanism 51 includes a flow meter or sensor 51a and a needle valve 51b. The flow rate to each cartridge 4a' or 4b' may be adjusted by adjusting the needle valve 51b for each fluid path. This provides a mechanism for adjusting the flow to each of the individual hollow fiber cartridges 4'. This is necessary because each cartridge 4' has a different resistance to flow. Media will take the path of least resistance. If no adjustments were possible, one cartridge could receive more flow than another and cells in the other cartridge 4' could be denied the favorable growth environment afford the cells in the cartridge 4' get the greatest flow. Furthermore, as cells grow asynchronously in the various individual cartridges 4', changes in resistance occur over time and require adjustment of the flow to assure equal perfusion in each cartridge 4' so that balanced cell growth may occur. It will be appreciated, that each plurality of cartridges 4', may include any practical number of cartridges permitted by the fluid dynamics of any alternate embodiments the cell growing device 2' of the present invention.

The solenoid valves 40a' and 40b' force an influx media coming into a lumen 20' from a respective inflow opening 16' to ultrafiltrate through the hollow fiber membranes or capillary walls 15' into the ECS 10' when they are closed. The ultrafiltrative flow rate is controlled by increasing or decreasing speed of the centrifugal pump 44b. Preferably, constant lumenal pressure is maintained. The lumenal pressure is monitored by in-line fluid pressure sensors 72. Preferably, all the variable aspects of the industrial scale device 2' are automated or controlled by the computer control mechanism 36' which may be supplied with an emergency power back-up system (not shown). The control system 36' preferably switches the three-way valves 42' and 54', and switches the solenoid valves 40a' and 40b' from open to closed and from closed to open, simultaneously on a regular schedule. Preferably the cycle switches, and the direction of the flow in the ECS connecting mechanism 8' reverses every ten minutes. Alternately, aspects of the device, which could otherwise be controlled by the computer, may be manually adjusted.

Independent control of pH and oxygen concentration ($O_2$) is accomplished by controlling the concentration of ($CO_2$) and ($O_2$) entering the individual gas cartridges 30, 30' and 74. A computer controlled stepper motor 80c is mechanically connected to each of the needle valves 80b controlling the flow rates of each of the three gases. The ($CO_2$) concentration is raised to lower pH and lowered to raise pH. The $N_2$ concentration is adjusted up or down to maintain a constant flow rate of the three gas mixture. However, if the ($CO_2$) concentration reaches zero and the pH is still falling, the computer 26' will increase the gas flow rate by proportionately increasing $N_2$ and $O_2$ flow rates. This will allow a greater amount of ($CO_2$) to diffuse out of the media, thereby lowering the pH thereof. If this is not sufficient to maintain the pH at a desired level, the rate at which fresh media is fed into the media reservoir 63 is increased either manually or, preferably, as directed by the computer control mechanism 36'. Oxygen ($O_2$) concentration is controlled in a similar manner. As more $O_2$ is demanded, the computer 26' will increase the $O_2$ flow rate and decrease the $N_2$ flow rate.

The cells 22 that are to be expanded in the cartridges 4 are inoculated through the septum 11 on the port 24 in the housing 12 with a syringe. If cells are the final product, they are harvested from the cartridges 4 by utilizing a Haemonetics V50 aphoresis instrument. A custom tubing set is connected to the inoculation port 24 of each cartridge or bioreactor 4. Cells 22 are forced out of the cartridges 4 under ultrafiltrative force. The cells are captured in the centrifuge of the aphoresis instrument, while the flushing media is diverted to a 10 liter waste bag. The cells 22 may then be washed and resuspended for further use. This cell harvest procedure has the advantage of being a completely closed system, thereby minimizing the risk of contamination.

Referring now also to FIG. 6, the device 2' may be prepared for an in-line sterilization procedure by removing certain parts that cannot withstand high temperatures and replacing them with temporary parts that can. For instance, the hollow fiber cartridges 4' and adjacent filters 28', and the gas transfer cartridges 30, 30' and 74 are removed and replaced by stainless steel tubing parts 92 and 93, respectively, which are designed to fit the spaces left unconnected by the removal of the aforementioned parts. Once the stainless steel tubing parts 92 and 93 are in place, and the flexible tubes 84 and 85 have been removed and the caps 84b and 85b are in place, steam is pumped into the inlet valve 90 at 15 psi. The steam is pumped in through a sterilization steam filter 78 and is allowed to circulate through the various fluid pathways by closing in-line valve 59a and opening the outlet valve 58 which is equipped with a sterilization steam filter 78. The steam is preferably generated in a commercial steam generator which preferably generates steam from low-endotoxin water for injection (e.g. H200 generator from Finn Agua, Inc., Seattle, Wash.). The sterilization steam filters 78 through which the steam enters and leaves the system are preferably 0.2 micron steam filters.

A pressure gauge 91 makes it possible to monitor the steam pressure so that a pressure of 15 psi may be maintained. In addition, a pressure relief valve 62, having a 15 psi pressure relief rating and equipped with a sterilization steam filter 78, is provided to insure that the pressure does not exceed 15 psi. The steam is allowed to circulate throughout the system. Temperature is preferably monitored at approximately 18 inch intervals, or at each contortion in the various pathways, by the temperature monitoring mechanisms 73. Steam is preferably circulated at 15 psi for 30 minutes. Temperature is monitored and the time is not counted unless all temperature monitors exceed 121° C. In an alternate embodiment the sterilization process is automated and computer controlled.

Preferably, the hollow fiber cartridges 4 of the present invention have a length greater than about four inches, more preferably greater than about five inches and even more preferably greater than about six inches. Alternate embodiments of the present invention may be equipped with hollow fiber cartridges 4 which have a length of about eight inches or more. It will be appreciated that, when used with the present invention, hollow fiber cartridges 4 having even greater lengths will provide even greater space for cell growth. Therefore, it is considered to be desirable to have hollow fiber cartridges 4 which may even exceed a length of about 10–12 inches.

It will be appreciated that any type of cell which can grow in a cell culturing device, can be cultured or grown in the cell growing devices of the present invention. The cells which may be grown in the cell growing devices of the present invention include, but are not limited to the following classes of cells: mammalian cells, plant cells, microbiological cells and other single cell organisms, such as bacteria, fungi, and algae, and the like. The mammalian cells include anchorage dependent cells or suspension or floating cells. These cells may be primary cells, transformed cells, neoplastic cells, cells altered by recombinant DNA techniques, fused cells, including mammalian cells fused with other types of cells or with other mammalian cells, cells which have been otherwise altered by natural or artificial means, and the like. The plant cells include normal plant cells, transformed or otherwise altered cells, cells altered by recombinant DNA techniques, fused cells and the like. The microbial or other single cell organisms also include a variety of transformed or otherwise altered cells including, but not limited to, cells or organisms altered by recombinant DNA techniques, fusion, or the like.

Although the present invention has been described with reference to preferred embodiments, workers skilled in the art will recognize that changes may be made in form and detail without departing from the spirit and scope of the invention.

What is claimed is:

1. A cell growing device for in vitro cell population growth, the cell growth occurring in fluid growth media within the device, the device comprising:

a first hollow fiber cartridge having a housing and a plurality of capillaries, each of the capillaries including walls having interiors and exteriors, the housing having a first inflow opening and a first outflow opening, the plurality of capillaries extending between the first inflow opening and first outflow opening, at least one of the capillaries having selectively permeable walls, the interiors of the walls of the plurality of capillaries defining a first lumen extending between and being in fluid communication with the first inflow and the first outflow openings, the exteriors of the walls of the plurality of capillaries and the housing defining a first extracapillary space, the housing having a first primary orifice in fluid communication with the first extracapillary space;

an outflow blocking mechanism for substantially blocking a flow of media from the first lumen via the first outflow opening, wherein the outflow blocking mechanism can be closed to substantially block the flow of media from the first lumen via the first outflow opening such that substantially all of the influx of media into the first lumen via the first inflow opening is directed across the capillary walls into the first extracapillary space; and an extracapillary space monitoring mechanism for monitoring and directly adjusting the oxygen concentration and the pH of the media located in the first extracapillary space.

2. The cell growing device of claim 1, wherein the outflow blocking mechanism can be alternately opened and closed such that the flow of media from the first lumen via the first outflow opening is alternately permitted and substantially blocked.

3. The cell growing device of claim 2, wherein the outflow blocking mechanism includes a first valve in fluid communication with the first outflow opening distal to the first lumen, wherein the first valve can be alternately opened and closed such that the flow of media from the first lumen via the first outflow opening is alternately permitted and substantially blocked.

4. The cell growing device of claim 3, wherein the device includes a controlling computer, the controlling computer being programmed to alternately switch the first valve open and closed.

5. The cell growing device of claim 4, wherein the extracapillary space monitoring mechanism includes a gas transfer mechanism for exchanging gas across a membrane separating the media from a controlled gaseous environment within the gas transfer mechanism, the device including a gas delivery mechanism for delivering specific gases to the controlled gaseous environment, the specific gases including oxygen gas, carbon dioxide, nitrogen gas, or combinations thereof.

6. The cell growing device of claim 1, wherein at least one of the capillaries having the selectively permeable walls has a molecular weight cut-off of equal to or less than about 30,000 daltons.

7. A process for the in vitro growth of cells comprising:
depositing a first plurality of cells in a first extracapillary space of a first hollow fiber cartridge, wherein the first hollow fiber cartridge has a housing and a plurality of capillaries, each of the capillaries including walls having interiors and exteriors, the housing having a first inflow opening and a first outflow opening, the plurality of capillaries extending between the first inflow opening and the first outflow opening, at least one of the capillaries having selectively permeable walls, the interiors defining a first lumen extending between and being in fluid communication with the first inflow opening and the first outflow opening, the exteriors and the housing defining the first extracapillary space, the housing having a first primary orifice in fluid communication with the first extracapillary space;
supplying the first plurality of cells with nutrient media through a first flow path extending from the first inflow opening to the first primary orifice; and
oxygenating the first plurality of cells by flowing oxygenated media through a second flow path extending from the first primary orifice to the first outflow opening, wherein substantially blocking the flow of media from the first lumen via the first outflow opening and causes substantially all of the influx of media into the first lumen via the first inflow opening to be directed across the capillary walls into the first extracapillary space.

8. The process of claim 7, wherein a first valve in fluid communication with the first outflow opening distal to the first lumen alternately permits and substantially blocks flow of media from the first lumen via the first outflow opening.

9. The process of claim 8, and further comprising:
depositing a second plurality of cells in a second extracapillary space of a second hollow fiber cartridge, wherein the second hollow fiber cartridge has a housing and a plurality of capillaries, each of the capillaries including walls having interiors and exteriors, the housing having a second inflow opening and a second outflow opening, the plurality of capillaries extending between the second inflow opening and the second outflow opening, at least one of the capillaries having selectively permeable walls, the interiors defining a second lumen extending between and being in fluid communication with the second inflow opening and the second outflow opening, the exteriors and the housing defining the second extracapillary space, the housing having a second primary orifice in fluid communication with the second extracapillary space;
supplying the second plurality of cells with nutrient media through the second flow path further extending from the second inflow opening to the second primary orifice; and
oxygenating the second plurality of cells by flowing oxygenated media through the first flow path further extending from the second primary orifice to the second outflow opening.

10. The process of claim 9, wherein a second valve in fluid communication with the second outflow opening distal to the second lumen alternately permits or substantially blocks flow of media from the second lumen via the second outflow opening.

11. The process of claim 10, and further comprising fluidly connecting the first and second hollow fiber cartridges with a fluid connecting mechanism, the fluid connecting mechanism including a recirculation mechanism for recirculating fluid media from the respective outflow openings of the hollow fiber cartridges to inflow openings thereof and an extracapillary space connecting mechanism for fluidly connecting the first extracapillary space with the second extracapillary space, wherein the recirculation mechanism includes the first valve and the second valve, and wherein all fluid communication between the first cartridge and the second cartridge other than that passing through the recirculation mechanism passes through the extracapillary space connecting mechanism.

12. The process of claim 11, wherein the extracapillary space connecting mechanism includes a connecting chamber in fluid communication with the first primary orifice and the second primary orifice, wherein the connecting chamber provides fluid communication between the first extracapillary space and the second extracapillary space, and wherein the connecting chamber including a monitoring mechanism for monitoring the oxygen concentration and pH of the media therein.

13. The process of claim 12, and further comprising exchanging gas across a membrane separating the media from a controlled gaseous environment for delivering specific gases to the cells, wherein the specific gases includes oxygen gas, carbon dioxide, nitrogen gas, or combinations thereof.

14. The process of claim 10, and further comprising controlling the operation of the first and second valves using a controlling computer, wherein the controlling computer is programmed to simultaneous open one of the first and second valves and close the other, thereby alternately switching the first and second valves from open to closed and from closed to open in a reciprocal relationship wherein one of the first and second valves is always open and one is always closed.

15. The process of claim 14, wherein a third valve alternately directing media from the recirculation mechanism to the first lumen or second lumen via the respective proximate inflow opening, the third valve being connected to and controlled by the controlling computer, the controlling computer being programmed such that the media from the recirculation means is alternately directed to either the first lumen or second lumen at the same time that the flow of media from that respective lumen is substantially blocked by the closure of the respective first valve or the second valve.

16. The process of claim 7, and further comprising monitoring and adjusting the oxygen concentration and the pH of the media located in the first extracapillary space.

17. The process of claim 7, wherein the selectively permeable walls have a molecular weight cut-off of equal to or less than about 30,000 daltons.

18. A process for the in vitro growth of cells comprising:
depositing a first plurality of cells in a first extracapillary space of a first hollow fiber cartridge, wherein the first hollow fiber cartridge has a housing and a plurality of capillaries, each of the capillaries including walls having interiors and exteriors, the housing having a first inflow opening and a first outflow opening, the plurality of capillaries extending between the first inflow opening and the first outflow opening, at least one of the capillaries having selectively permeable walls, the interiors defining a first lumen extending between and being in fluid communication with the first inflow opening and the first outflow opening, the exteriors and the housing defining the first extracapillary space, the housing having a first primary orifice in fluid communication with the first extracapillary space;

depositing a second plurality of cells in a second extracapillary space of a second hollow fiber cartridge, wherein the second hollow fiber cartridge has a housing and a plurality of capillaries, each of the capillaries including walls having interiors and exteriors, the housing having a second inflow opening and a second outflow opening, the plurality of capillaries extending between the second inflow opening and the second outflow opening, at least one of the capillaries having selectively permeable walls, the interiors defining a second lumen extending between and being in fluid communication with the second inflow opening and the second outflow opening, the exteriors and the housing defining the second extracapillary space, the housing having a second primary orifice in fluid communication with the second extracapillary space;

supplying the first plurality of cells with nutrient media through a first flow path extending from the first inflow opening to the first primary orifice;

oxygenating the second plurality of cells by flowing oxygenated media through the first flow path extending from the second primary orifice to the second outflow opening;

supplying the second plurality of cells with nutrient media through a second flow path extending from the second inflow opening to the second primary orifice; and oxygenating the first plurality of cells by flowing oxygenated media through the second flow path extending from the first primary orifice to the first outflow opening.

19. The process of claim 18, and further comprising fluidly connecting the first and second hollow fiber cartridges with a fluid connecting mechanism, the fluid connecting mechanism including a recirculation mechanism for recirculating fluid media from the respective outflow openings of the hollow fiber cartridges to inflow openings thereof and an extracapillary space connecting mechanism for fluidly connecting the first extracapillary space with the second extracapillary space, wherein all fluid communication between the first cartridge and the second cartridge other than that passing through the recirculation mechanism passes through the extracapillary space connecting mechanism.

20. The process of claim 19, wherein a first valve in fluid communication with the first outflow opening distal to the first lumen alternately permits or substantially blocks flow of media from the first lumen via the first outflow opening and wherein a second valve in fluid communication with the second outflow opening distal to the second lumen alternately permits or substantially blocks flow of media from the second lumen via the second outflow opening.

21. The process of claim 20, and further comprising controlling the operation of the first and second valves using a controlling computer, wherein the controlling computer is programmed to simultaneous open one of the first and second valves and close the other, thereby alternately switching the first and second valves from open to closed and from closed to open in a reciprocal relationship wherein one of the first and second valves is always open and one is always closed.

22. The process of claim 21, wherein a third valve alternately directing media from the recirculation mechanism to the first lumen or second lumen via the respective proximate inflow opening, the third valve being connected to and controlled by the controlling computer, the controlling computer being programmed such that the media from the recirculation means is alternately directed to either the first lumen or second lumen at the same time that the flow of media from that respective lumen is substantially blocked by the closure of the respective first valve or the second valve.

23. The process of claim 19, wherein the extracapillary space connecting mechanism includes a connecting chamber in fluid communication with the first primary orifice and the second primary orifice, wherein the connecting chamber provides fluid communication between the first extracapillary space and the second extracapillary space, and wherein the connecting chamber including a monitoring mechanism for monitoring the oxygen concentration and pH of the media therein.

24. The process of claim 23, and further comprising exchanging gas across a membrane separating the media from a controlled gaseous environment for delivering specific gases to the cells, wherein the specific gases includes oxygen gas, carbon dioxide, nitrogen gas, or combinations thereof.

* * * * *